US007166627B2

(12) United States Patent
Day et al.

(10) Patent No.: US 7,166,627 B2
(45) Date of Patent: Jan. 23, 2007

(54) ANTIBIOTIC COMPOSITIONS AND METHODS OF USING THE SAME

(75) Inventors: Richard A. Day, Cleves, OH (US); Charles Thomas Rentz, Cincinnati, OH (US); Gregory Shannon Huang, Cincinnati, OH (US); Amit B. Patel, Galloway, OH (US); Amjad M. Iqbal, Cincinnati, OH (US); Paul M. Gretz, Cincinnati, OH (US); Xiangzhong Shen, West Chester, PA (US); Xuefei Cao, Los Angeles, CA (US)

(73) Assignee: University of Cincinnati, Cincinnati, OH (US)

( * ) Notice: Subject to any disclaimer, the term of this patent is extended or adjusted under 35 U.S.C. 154(b) by 235 days.

(21) Appl. No.: 10/641,427

(22) Filed: Aug. 15, 2003

(65) Prior Publication Data

US 2004/0254381 A1 Dec. 16, 2004

Related U.S. Application Data

(60) Provisional application No. 60/404,184, filed on Aug. 16, 2002.

(51) Int. Cl.
*A61K 31/42* (2006.01)
*C07D 261/02* (2006.01)
(52) U.S. Cl. .................................. 514/380; 548/243
(58) Field of Classification Search ............... 548/243; 514/380
See application file for complete search history.

(56) References Cited

U.S. PATENT DOCUMENTS 5,066,665 A * 11/1991 Hobbs ..................... 514/380

OTHER PUBLICATIONS

Abramski, Wojciech and Chmielewski, Marke, Practical Synthesis of Sinigrin, J. Carbohydrate Che. 15(1) (1996) pp. 109-113.
Ahluwalia, Ritu et al., A Bifunctional Monocyclic β-Lactam Cross-links Across the Active Site of β-Lactamase, Biochemical and Biophysical Research Communications, vol. 206, No. 2 (1995) pp. 577-583.
Ahmad, Muhammad et al., Clinical Characteristics and Molecular Epidemiology Associated with Imipenem-Resistant *Kiebsiella pneumoniae*, Clin. Infect. Dis. 29 (1999) pp. 352-355.

Baldwin, Jack E. et al., A General Procedure for the Synthesis of Isoxazolidin-5-ones, Tetrahedran, vol. 40, No. 21, (1984) pp. 4363-4370.
Baldwin, Jack E. et al., Synthesis of Chiral Isoxazolidin-5-ones and Their Applications to the Synthesis of -(N-Hydroxyamini)-Alaninines. Tetrahedron, vol. 50, No. 17 (1994) pp. 5049-5066.
Frelek, Jadwiga et al., Synthesis, Structure and Chiroptical Properties of Isoxazolindin-5-ones, Tetrahedron Asymmetry, vol. 7 No. 12 (1996) pp. 3415-3426.
Jungheim, L.N. and Temansky, R.J., Non-β-lactam mimics of β-lactam antibiotics, The Chemistry of β-lactam (1992) pp. 306-324.
Jurczak, Margarita et al., Isoxazolidin-5-one—Isoxazolidine Rearrangement, an Entry to 3-Amino-3-deoxy Sugars, Tetrahedron, vol. 52, No. 4 (1996) pp. 1411-1424.
Kemodle, Douglas S., Mechanisms of Resistance to β-lactam Antibiotics, Gram-Positive Pathogens, ed. by V.A. Fischetti et al., American Society for Microbiology, Washington, D.C. (2000) pp. 609-620.
Koch, Arthur L., Penicillin Binding Proteins, β-Lactams, and Lactamases: Offensive, Attacks and Defensive Countermeasures. Critical Reviews in Microbiology, 26(4), pp. 205-220 (2000).
Liguori, Angelo et al., N,O-Heterocycles. XIX. The Formation of the Isoxazolidin-5-one Ring from Cinnamohydroxamic Acid Derivatives, Gazzetta Chimica Italiana, 116 (1986) pp. 377-380.
Livermore, David M., Antiobiotic resistance in staphylococci, International Journal of Antimicrobial Agents, 16 (2000) pp. S3-S10.
Livermore, David M., Of Pseudomonas, porins, pumps and carbapenems, Journal of Antimicrobial Chemotherapy (2001) 47, pp. 247-250.
Maciejewski, Sylvester et al., An Approach to Carbapenems from α β-Unsaturated Sugar Lactones, Tetrahedron, vol. 48, No. 47 (1992) pp. 10363-10376.
Merino, Pedro et al., Lewis acid stereocontrolled additions of a silyl ketene acetal to 2,3-di-O-isoropylidene-D-glyceraldehyde nitrones. Synthesis of L-isoxazolidinyl nucleosides, Tetrahedron Letters 41 (2000) pp. 9239-9243.
Merino, Pedro et al., Synthesis of isoxazolidin-5-ones via stereo controlled Michael additions of benzylhydroxylamine to L-serine derived α β-unsaturated esters, Tetrahedron: Asymmetry 9 (1998) pp. 3945-3949.
Nozaki, Y. et al., Binding of a non- β-lactam antibiotic to penicillin-binding proteins, nature, 325 (1987) pp. 179-180.

(Continued)

*Primary Examiner*—Kamal A. Saeed
(74) *Attorney, Agent, or Firm*—Frost Brown Todd LLC

(57) ABSTRACT

The present invention relates to a process for the production of substituted 5-isoxazolidinone antibiotics. More specifically the patent relates to the production of compounds that mimic the antibiotic action of β-lactams, are resistant to β-lactamase degradation, and inhibit all classes of β-lactamase.

7 Claims, No Drawings

OTHER PUBLICATIONS

Panfil, I. et al., α β-Unsaturated Sugar δ-Lactones: Preparation and Conjugate Addition of Hydroxylamines and Hydra zines. Polish J. Chem. 73 (1999) pp. 1099-1110.

Panfil, Irma et al., Isoxazolidin-5-one analogs of β-lactam antibiotics, Carbohydrate Research, 306 (1998) pp. 505-515.

Panfil, Irma et al., Synthesis of Enantiomerically Pure 2.3-Disubstituted Isoxazolidin-5-Ones, Tetrahedron Letters, vol. 30, No. 12 (1998) pp. 1527-1528.

Pearson, Clay et al., Enantiospecific Synthesis of N-Bod-Adda: A linear Approach, Organic Letters, vol. 2, No. 18 (2000) pp. 2901-2903.

Rahal J.J., Extended-spectrum β-lactamases: how big is the problem?, Clin. Microbial Infect. 2000: 6 (Supplement 2) pp. 2-6.

Singh, Janak et al., Desulfation and Rearrangement of Tigemonam to an Isoxazolidin-5-one and the Synthesis of the Rearrangement product, J. Hererocyclic Chem., 26 (1998) pp. 17-21.

Socha, Dariusz et al., Stereocontrolled Entry to Negamycin from D-Glucose, Tetrahedron Letters, vol. 36, No. 1 (1995) pp. 135-138.

Socha, Darlusz et al., Synthesis of Acosamine and Daunasamine from Sugar δ-Enelactones, Tetrahedrone, vol. 53, No. 2 (1997) pp. 739-746.

Stamm, H. and Hoenicke, J., Archiv. Pharm. (Weinheim) 305 (1972) pp. 359-368.

Stamm, Helmut and Steudle, Harald, Arch. Pharm. (Weinheim) 310 (1997) pp. 873-881.

Thompson, Kenneth S. and Moland, Ellen Smith, Version 2000: the new β-lactamases of gram-negative bacteria at the dawn of the new millennium, Microbes and Infection, 2 (2000) pp. 1225-1236.

* cited by examiner

ANTIBIOTIC COMPOSITIONS AND METHODS OF USING THE SAME

CROSS REFERENCE TO RELATED APPLICATIONS

This application claims priority under 35 U.S.C. 119 to U.S. provisional application Ser. No. 60/404,184, filed Aug. 16, 2002, and entitled "Antibiotic Compositions and Methods of Using The Same," the disclosure of which is hereby expressly incorporated herein by reference.

FIELD OF THE INVENTION

The present invention relates to a process for the production of substituted 5-isoxazolidinone antibiotics. More specifically the patent relates to the production of compounds that mimic the antibiotic action of β-lactams, are resistant to β-lactamase degradation, and inhibit all classes of β-lactamase. In one embodiment, the present invention relates to the synthesis of novel appropriately substituted 5-isoxazolidinones (hereinafter collectively referred to as 5ISOX) and their use as antibiotics.

BACKGROUND OF THE INVENTION

The purpose of this invention is to provide a non-β-lactam mimic of the β-lactam antibiotics that target bacterial metabolic pathways; no analogous pathways are found in animals or plants. This is considered to be advantageous therapeutically because it minimizes interference(s) with the metabolism of the object of treatment.

The challenges to β-lactam antibiotics are increasing to the point that there is a fear that an unacceptably long list of pathogens may arise that are totally resistant to the pharmaceutically useful β-lactams as well as other antibiotics. See Thomson and Moland, Microbes and Infection 2, 1225–1236 (2000); Koch, Critical Rev. Microbiol. 26, 205–220 (2000); Emerging Drugs 5, 347–365 (2000); Kemodle, "Mechanisms of Resistance to β-Lactam Antibiotics" in Gram Positive Pathogens 609–620 (2000).

The last two decades have seen major changes in the types of β-lactamase production by which Gram-negative bacteria protect themselves from β-lactam antibiotics; this has occurred mainly by gene transfer and mutation. Changes have affected the responses to β-lactams in two significant ways; the production of novel β-lactamases with new substrate or β-lactamase inhibitor interactions, and the production of multiple β-lactamases. The result is an increasing number of pathogens, many of them nosocomial, with less predictable responses to β-lactam therapy, and which are sometimes not dependably indicated by routine antibiotic susceptibility tests. If laboratories do not detect new types of resistance, infected patients are put at risk. Some of the novel β-lactamases (the main cause of β-lactam resistance) have interchangeable chromosomal and plasmid-mediated genes; this promiscuity makes them capable of wide dissemination and confers the potential for epidemic problems. In some pathogens the effects of relatively weak β-lactamases may be augmented by other resistance mechanisms, producing synergistic effects in which the β-lactamases have a greater impact than anticipated. An increasing number of pathogens with a multiplicity of resistance mechanisms are appearing. This has created more multiple resistant, and sometimes totally resistant, pathogens. See Ahmad et al., Clin Infect. Dis. 29, 325–355 (1999). In a specific case the preferred use of carbapenems against Pseudomonas, runs the risk that resistance will develop against these useful β-lactams. See Livermore, J. Antimicrobial Chemotherapy 47, 247–250 (2001).

Novel important β-lactamases fall into four groups. These are 1) Extended spectrum β-lactamase (ESBLs), 2) β-lactamases with reduced sensitivity to β-lactamase inhibitors. 3) Plasmid-mediated AmpC β-lactamase, and 4) Carbapenem-hydrolyzing β-lactamases.

Increased bacterial resistance to β-lactams will continue to plague modem medicine. The unfortunate changes that have occurred in the types of β-lactamase production are themselves a consequence of the selection pressure created by antibiotic usage. Unpredictable responses of bacteria will undoubtedly continue to surprise us with increasing resistance to β-lactam antibiotics. See Livermore, op. cit. It seems inevitable that the most important threats to medicine will be more frequent encounters with pathogens that produce many β-lactamases including potent plasmid-mediated β-lactamases such as the extended spectrum β-lactamases, AmpC related β-lactamases, and metallo-β-lactamases. These β-lactams increase resistance. The latter are particularly alarming with their resistance to β-lactamase inhibitors in current pharmaceutical use. Also, all ESBLs are a challenge to β-lactam antibiotic usage. See Rahal, Clinical Microbiol. Infection 6 (suppl 2) 2–6 (2000). The inability of many clinical microbiology laboratories to provide timely and accurate information about the occurrence of such enzymes will further exacerbate their spread. In the face of all this, the spread of resistance will continue and there will be more bacteria that are resistant to currently available antibiotics. To avoid this it will be necessary to change current therapeutic and diagnostic approaches and to find novel antibiotics not affected by the increasing resistance to β-lactams.

A specific example of a major challenge to β-lactam antibiotics is the Gram T, resistant staphylococci. While the wild type staphylococci are susceptible to the β-lactans, they are an increasing source of morbidity and mortality in the nosocomial setting. Hospitals are plagued by resistant strains that represent a serious health hazard. See Livermore, International Journal of Antimicrobial Agents 16, S3–S10 (2000).

BRIEF SUMMARY OF THE INVENTION

The present invention relates to the preparation of various 5-isoxazolidinones (5ISOX), appropriately substituted in the 2, 3, and 4 positions, formula II, and their use as antibiotics and inhibitors of β-lactamases of all classes.

Specifically, the present invention relates to antimicrobial compounds and methods of using the compounds comprising administering an antimicrobial amount of a composition comprising a specifically defined nontoxic, 5-isoxazolidinone or 5-isoxazolidinone derivative.

The invention relates to a method of preparing compounds of the formula II and to pharmaceutically acceptable salts thereof. The compounds of formula II are antibacterial agents that may be used to treat various bacterial infections. The invention also relates to pharmaceutical compositions containing the compounds of formula II and to methods of treating bacterial infections by administering the compounds of formula II. The invention also relates to methods of preparing the compounds of formula III and to intermediates useful in such preparation.

This invention also relates to pharmaceutical compositions containing the novel compounds, and to methods of treating bacterial infections and protozoa infections in mammals, fish and birds by administering the novel compounds to mammals, fish and birds requiring such treatment.

Specifically, the invention relates to a method of preparing antibacterial 5-isoxazolidinone compounds comprising reacting (a) an N-substituted hydroxylamine having the general formula $R_1NHOH$; and (b) a hydrogen form of formylated Leuchs anhydride of glycine having the general formula (I):

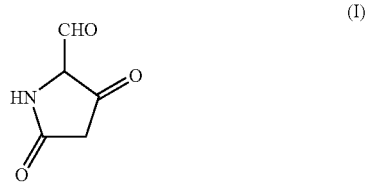

(I)

in the presence of a solvent of pyridine and an alcohol having the general formula $R_2OH$;

for sufficient time and at sufficient temperature and pH to allow the formation of a 5-isoxazolidinone compound, enantiomer, diastereomer or pharmaceutically acceptable salt thereof having the general formula (II):

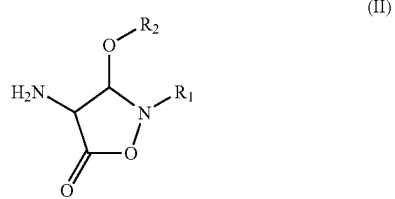

(II)

wherein $R_1$, and $R_2$, are the same or different, selected from the group consisting of: (a) hydrogen; (b) alkyl, aryl, aralkoxy, aralkyl, cycloalkyl, alkynyl, alkenyl, alkoxy, carboxy, carbalkoxy, carbalkoxyalkyl, carbamoyl, carbamoylalkyl, hydroxy, hydroxyalkyl, acyl, carbamoyloxy, acyloxy, aryloxy, alkylthio, alkylsulfinyl, cycloalkyl, cycloalkylalkyl, cycloalkenyl, cycloalkenylalkyl, among other groups, each which may be saturated and unsaturated and each which may be substituted with $Z_1$, $Z_2$ and $Z_3$; (c) halogen; (d) hydroxyl; (e) cyano; (f) nitro; (g) —C(O)H or —C(O)$R_6$; (h) —$CO_2H$ or —$CO_2R_6$; (i) -$Z_4$—$NR_7R_8$; or (j) -$Z_4$—$N(R_{11})$ -$Z_5$—$NR_9R_{11}$;

wherein $R_6$, $R_7$, $R_8$, $R_9$, $R_{10}$ and $R_{11}$, are each independently (a) hydrogen; or (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z_1$, $Z_2$ and $Z_3$;

wherein $Z_1$, $Z_2$ and $Z_3$ are each independently (a) hydrogen; (b) halo; (c) hydroxy; (d) alkyl; (e) alkenyl; (f) aryl; (g) aralkyl; (h) alkoxy; (i) aryloxy; (j) aralkoxy; (k) heterocycle, substituted heterocycle or heterocyclooxy; (l) —SH, —S(O)n $Z_4$, —S(O)m —OH, —S(O)m —$OZ_4$, —O—S(O)m -$Z_4$, —O—S(O)m OH or —O—S(O)m —$OZ_4$; (m) oxo; (n) nitro; (o) cyano; (p) —C(O)H or —C(O) $Z_4$; (q) —$CO_2H$ or —$CO_2$ $Z_4$; and wherein $Z_4$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy, trihaloalkoxy, dialkylaminocarbonyl, alkylcarbonylamino, arylalkoxy, aryloxyalkyl, alkylaryloxyalkyl and heterocycle; and substituted compounds thereof.

Preferably, wherein the 4-amino group of the 5-isoxazolidinone compound is further modified by reacting with a compound having the general formula $R_3YX$ for sufficient time and at sufficient temperature to allow the formation of a 5-isoxazolidinone derivative compound, enantiomer, diastereomer or pharmaceutically acceptable salt thereof, having the general formula (III):

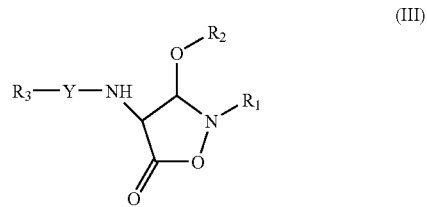

(III)

wherein $R_3$ is the selected from the group consisting of: (a) hydrogen; (b) alkyl, aryl, aralkoxy, aralkyl, cycloalkyl, alkynyl, alkenyl, alkoxy, carboxy, carbalkoxy, carbalkoxyalkyl, carbamoyl, carbamoylalkyl, hydroxy, hydroxyalkyl, acyl, carbamoyloxy, acyloxy, aryloxy, alkylthio, alkylsulfinyl, cycloalkyl, cycloalkylalkyl, cycloalkenyl, cycloalkenylalkyl, among other groups, each which may be saturated and unsaturated and each which may be substituted with $Z_1$, $Z_2$ and $Z_3$; (c) halogen; (d) hydroxyl; (e) cyano; (f) nitro; (g) —C(O)H or —C(O)$R_6$; (h) —$CO_2H$ or —$CO_2R_6$; (i) -$Z_4$—$NR_7R_8$; or (j) -$Z_4$ —$N(R_{11})$ -$Z_5$—$NR_9R_{11}$;

wherein $R_6$, $R_7$, $R_8$, $R_9$, $R_{10}$ and $R_{11}$, are each independently (a) hydrogen; or (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z_1$, $Z_2$ and $Z_3$;

wherein $Z_1$, $Z_2$ and $Z_3$ are each independently (a) hydrogen; (b) halogen; (c) hydroxy; (d) alkyl; (e) alkenyl; (f) aryl; (g) aralkyl; (h) alkoxy; (i) aryloxy; (j) aralkoxy; (k) heterocycle, substituted heterocycle or heterocyclooxy; (l) —SH, —S(O)n $Z_4$, —S(O)m —OH, —S(O)m —$OZ_4$, —O—S(O)m -$Z_4$, —O—S(O)m OH or —O—S(O)m —$OZ_4$; (m) oxo; (n) nitro; (o) cyano; (p) —C(O)H or —C(O) $Z_4$; (q) —$CO_2H$ or —$CO_2$ $Z_4$;

wherein $Z_4$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy, trihaloalkoxy, dialkylaminocarbonyl, alkylcarbonylamino, arylalkoxy, aryloxyalkyl, alkylaryloxyalkyl and heterocycle; or heterocycle or substituted heterocycle;

wherein X is selected from the group consisting of halogen and acyloxy; and wherein Y is selected from the group consisting of —CO, —$CH_2$, and —$SO_2$.

More preferably, the 5-isoxazolidinone compound is 3-alkoxy-5-isoxazolidinones, 3-aralkoxy-5-isoxazolidinones, 3-aroxy-5-isoxazolidinones or pharmaceutically acceptable salts thereof.

The invention also provides for pharmaceutical compositions of a compound of formula (II) or (III); a pharmaceutically acceptable salt thereof, or an in-vivo-hydrolysable ester thereof, and a pharmaceutically acceptable diluent or carrier. Collectively β-lactam antibiotics are a diverse array of chemical structures. This panoply includes cephalosporins, cephamycins, oxa- and carbacephems, penicillins, penems, carbapenems and monobactams. Each is capable of acylating the penicillin binding proteins (PBPs) thus interfering with bacterial cell-wall biosynthesis and maintenance of the integrity of the cell wall synthesizing complex. A clinically useful β-lactam must be able to penetrate the bacterial cell wall, and resist hydrolysis by β-lactamases in order to inactivate the target PBPs. Low incidence of side effects, occurring with the potent antibacterial activity displayed by the β-lactams, makes them attractive structures to emulate in the search for new antibacterial agents effective against the resistant strains; this patent describes such an emulation.

The pharmacophore of active β-lactam antibiotics is a sufficiently reactive azetidinone, shown below, which possesses the correct molecular shape for binding to the target PBPs. The acylating ability of the β-lactam moiety is similar among biologically active cephalosporins or penicillins. It is now clear that the β-lactam ring itself is responsible for antibacterial activity.

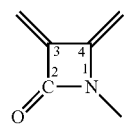

Previous attempts to prepare biologically active γ- or δ-lactam mimics of penicillin met with failure. See Jungheim and Ternansky, in Page *The Chemistry of β-lactam*, pp. 306–324(1992). Either these compounds possessed insufficient chemical reactivity to acylate the PBPs and/or their molecular shape precluded a good fit in the active site of the PBPs. Possibly electron-withdrawing substituents at say C-3 might increase the acylating ability of a γ-lactam by delocalization of the lactam nitrogen or through an olefinic bond. Modeling studies supported the hypothesis that a γ-lactam could be designed to mimic a β-lactam with regard to chemical reactivity and molecular shape in spite of their well-documented chemical inertness. It is not known a priori if a γ-lactam can penetrate the bacterial cell wall. Both of these factors are critical to the ultimate success or failure of the potential antibacterial agent.

While variously substituted 5ISOX have been produced with the stated purpose of producing β-lactam analogs; none with significant in vitro antibiotic activity against *E. coli* or *S. aureus* was found. See Panfil et al. Carb. Res. 306, 505–515 (1998). They state, "It appears that cyclic hydroxylamine esters [sic], contrary to cyclic hydroxamic esters . . . , do not provide any structural element offering antibacterial activity." They are referring to 5ISOX derivatives. None of the 5ISOX in their studies include a 3-alkoxy, 3-aralkoxy or 3-aryloxy substituent.

Also relevant to the present invention is the finding that 3-isoxalidinones, (3ISOX) members of the lacticivin group (IIIa, IIIb) were found to be biological active. See Nozaki et al. Nature 325, 179–180 (1987). It should be

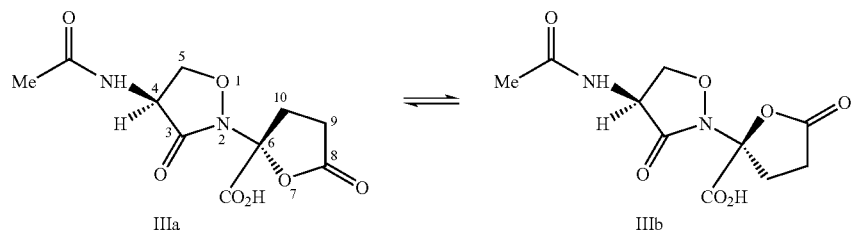

IIIa IIIb noted that 3ISOX have a chemistry distinct from 5ISOX.

The lack of a β-lactam ring in this antibiotic substance was significant. Lacticivin appeared to behave as though it contained a β-lactam ring, even though chemical analysis excluded the presence of such a functionality. The γ-lactam ring of lacticivin was found to act as a biological mimic of the β-lactam ring. Lacticivin binds to bacterial PBP1. See Nozaki et al. J. Antibiotics 42, 84–93 (1989). It displays greater activity against β-lactam-hypersensitive mutants when compared to parent strains. Lacticivin also interacts with β-lactamases. It is sensitive to these enzymes, and inhibits or induces an increase in the activity of the β-lactamases. These properties are all consistent with a β-lactam mode of action. In spite of the structural similarity to D-cycloserine, lacticivin's mode of action has been shown to be clearly distinct from it. The bacterial lethality of lacticivin is considered to be primarily due to inhibition of the PBPs. See Nozaki et al. (1989) op. cit. Finding a naturally occurring γ-lactam antibiotic that mimics the biological activity and mode of action of β-lactam antibiotics represents a step forward in the continuing development of antibacterial agents. Further modifications of the lacticivin nucleus, well may lead to the development of a γ-lactam antibacterial for use in clinical medicine. The 3-isoxazolidinones show that a suitability reactive five membered ring can mimic a β-lactam.

There are additional citations dealing with members of the chemical class of 5ISOX and their syntheses. These papers are concerned with their chemistry and not with antibacterial activity. See, e.g., Stamm and Hoenicke, Archiv. Pharm. (Weinheim) 305, 359–368 (1972); Stamm and Steudke ibid., 310, 873–881 (1977); Maciejewski et al, Tetrahedron 48, 10363–10376 (1992), Frelek et al., Tetrahedron Asymm. 7, 3415–3426 (1989); Jurczak et al., Tetrahedron 52, 1411–1424 (1996); Abramski and Chmielewski, J. Carb. Chem 15, 109–113 (1996); Merino et al., Tet. Lett. 41, 9239–9243 (2000); Socha et al., Tetrahedron 53, 739–746

(1997); Jurczak et al., ibid., 52 1411–1424 (1996); Socha et al., Tet. Lett. 36, 135–138 (1995); Baldwin et al., Tetrahedron 50, 5049–5066 (1994); Panfil et al., Pol. J. Chem. 73, 1099–1110 (1999); Jurczak et al., Synlett, 79–80 (1999); Merino et al., Tetrahedron Asymm. 9, 3945–3949 (1998); Panfil et al., Tet. Lett. 30, 1527–1528 (1989); Singh et al., J. Heterocycl. Chem. 26, 17–21 (1981); Liguori et al., Gazz. Chim. Ital. 116, 377–380 (1986); Baldwin et al., Tetrahedron 40, 4363–4370 (1984); Birch, D. Phil, Dissertation (Oxford) (1987); Pearson et al., Org. Lett. 2901–2903 (2000). None of the above refer to 3-alkoxy, 3-aralkoxy, nor 3-aroxy substituted 5ISOX.

DETAILED DESCRIPTION OF THE INVENTION

The present invention relates to the preparation of various appropriately substituted 5-isoxazolidinones (5ISOX) and demonstration of their anti-bacterial activity and ability to inhibit β-lactamases. Specifically, the present invention relates to antimicrobial compounds and methods of using the compounds comprising administering an antimicrobial amount of a composition comprising a specifically defined nontoxic, 5-isoxazolidinone or 5-isoxazolidinone derivative.

The invention relates to a method of preparing compounds of the formula II and to pharmaceutically acceptable salts thereof. The compounds of formula II are antibacterial agents that may be used to treat various bacterial infections. The invention also relates to pharmaceutical compositions containing the compounds of formula II and to methods of treating bacterial infections by administering the compounds of formula II. The invention also relates to methods of preparing the compounds of formula III and to intermediates useful in such preparation. As well as the 5-isoxazolidinone compound having antimicrobial activity prepared using the methods of the present invention including derivatives, enantiomers, diastereomers or pharmaceutically acceptable salts thereof.

This invention also relates to pharmaceutical compositions containing the novel compounds, and to methods of treating bacterial infections in mammals, fish and birds by administering the novel compounds to mammals, fish and birds requiring such treatment.

The methods of the present invention involves an improved synthesis of 5ISOX by reaction of appropriately N-mono-substituted hydroxylamines with 4-[1-oxalkyl]-2,5-oxazolidinediones (OOX) (Day and Wallace, U.S. Pat. No. 4,855,419),the structure of Formula I, and selected alcohols to produce variously substituted 5ISOX. In particular embodiments, 3-alkoxy, aralkoxy or aryloxy substituted 5ISOX are produced. A typical OOX is the formylated Leuchs anhydride of glycine (FLAG). A one-pot reaction then produces each 5ISOX. The simplicity of the synthesis is amenable to high throughput screening of 5ISOX for both antibiotic activity and β-lactamase inhibition.

In one embodiment, the formation of the 5ISOX is accomplished by a novel reaction of an N-substituted hydroxylamine having the general formula $R_1NHOH$, an alcohol having the general formula $R_2OH$ and the hydrogen form of formylated Leuchs anhydride of glycine (HFLAG), a 4-[1-oxalkyl]-2,5-oxazolidinedione (OOX) having the general formula (I):

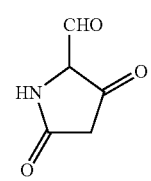

in the presence of pyridine to produce 5ISOX, or an enantiomer, diastereomer or pharmaceutically acceptable salt thereof, having the general formula:

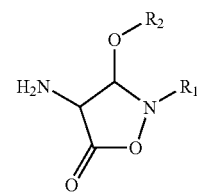

wherein $R_1$, and $R_2$, are the same or different, selected from the group consisting of: (a) hydrogen; (b) alkyl, aryl, aralkoxy, aralkyl, cycloalkyl, alkynyl, alkenyl, alkoxy, carboxy, carbalkoxy, carbalkoxyalkyl, carbamoyl, carbamoylalkyl, hydroxy, hydroxyalkyl, acyl, carbamoyloxy, acyloxy, aryloxy, alkylthio, alkylsulfinyl, cycloalkyl, cycloalkylalkyl, cycloalkenyl, cycloalkenylalkyl, among other groups, each which may be saturated and unsaturated and each which may be substituted with $Z_1$, $Z_2$ and $Z_3$; (c) halogen; (d) hydroxyl; (e) cyano; (f) nitro; (g) —C(O)H or —C(O)$R_6$; (h) —$CO_2H$ or —$CO_2R_6$; (i) -$Z_4$—$NR_7R_8$; or (j) -$Z_4$—$N(R_{11})$ -$Z_5$—$NR_9R_{11}$;

wherein $R_6$, $R_7$, $R_8$, $R_9$, $R_{10}$ and $R_{11}$, are each independently (a) hydrogen; or (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z_1$, $Z_2$ and $Z_3$;

wherein $Z_1$, $Z_2$ and $Z_3$ are each independently (a) hydrogen; (b) halo; (c) hydroxy; (d) alkyl; (e) alkenyl; (f) aryl; (g) aralkyl; (h) alkoxy; (i) aryloxy; (j) aralkoxy; (k) heterocycle, substituted heterocycle or heterocyclooxy; (l) —SH, —S(O)n $Z_4$, —S(O)m —OH, —S(O)m —$OZ_4$, —O—S(O)m -$Z_4$, —O—S(O)m OH or —O—S(O)m —$OZ_4$; (m) oxo; (n) nitro; (o) cyano; (p) —C(O)H or —C(O) $Z_4$; (q) —$CO_2H$ or —$CO_2$ $Z_4$; and wherein $Z_4$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy, trihaloalkoxy, dialkylaminocarbonyl, alkylcarbonylamino, arylalkoxy, aryloxyalkyl, alkylaryloxyalkyl and heterocycle; or heterocycle or substituted heterocycle.

The products of this reaction are then further chemically modified to obtain maximal antibacterial and β-lactamase inhibitory activity. Preferably, acylation, alkylation and/or sulfonylation further modify the 5ISOX. In one embodiment, the 4-amino group is modified by acylation, alkylation and/or sulfonylation with a compound having the general formula $R_3YX$ to produce a modified 5ISOX, or an enantiomer, diastereomer or pharmaceutically acceptable salt thereof, having the general formula (III):

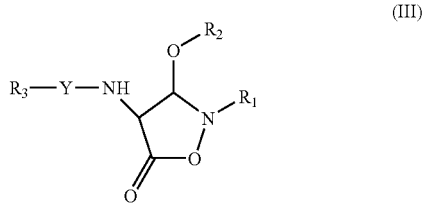

(III)

wherein $R_1$, $R_2$, and $R_3$ are the same or different, selected from the group consisting of: (a) hydrogen; (b) alkyl, aryl, aralkoxy, aralkyl, cycloalkyl, alkynyl, alkenyl, alkoxy, carboxy, carbalkoxy, carbalkoxyalkyl, carbamoyl, carbamoylalkyl, hydroxy, hydroxyalkyl, acyl, carbamoyloxy, acyloxy, aryloxy, alkylthio, alkylsulfinyl, cycloalkyl, cycloalkylalkyl, cycloalkenyl, cycloalkenylalkyl, among other groups, each which may be saturated and unsaturated and each which may be substituted with $Z_1$, $Z_2$ and $Z_3$; (c) halogen; (d) hydroxyl; (e) cyano; (f) nitro; (g) —C(O)H or —C(O)$R_6$; (h) —$CO_2H$ or —$CO_2R_6$; (i) -$Z_4$—$NR_7R_8$; or (j) -$Z_4$—$N(R_{11})$-$Z_5$—$NR_9R_{11}$;

wherein $R_6$, $R_7$, $R_8$, $R_9$, $R_{10}$ and $R_{11}$, are each independently (a) hydrogen; or (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z_1$, $Z_2$ and $Z_3$;

wherein $Z_1$, $Z_2$ and $Z_3$ are each independently (a) hydrogen; (b) halogen; (c) hydroxy; (d) alkyl; (e) alkenyl; (f) aryl; (g) aralkyl; (h) alkoxy; (i) aryloxy; (j) aralkoxy; (k) heterocycle, substituted heterocycle or heterocyclooxy; (l) —SH, —S(O)n $Z_4$, —S(O)m —OH, —S(O)m —O$Z_4$, —O—S(O)m -$Z_4$, —O—S(O)m OH or —O—S(O)m —O$Z_4$; (m) oxo; (n) nitro; (o) cyano; (p) —C(O)H or —C(O) $Z_4$; (q) —$CO_2H$ or —$CO_2$ $Z_4$;

wherein $Z_4$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy, trihaloalkoxy, dialkylaminocarbonyl, alkylcarbonylamino, arylalkoxy, aryloxyalkyl, alkylaryloxyalkyl and heterocycle; or heterocycle or substituted heterocycle;

wherein X is selected from the group consisting of halogen and acyloxy, among other groups; and wherein Y is selected from the group consisting of —CO, —$CH_2$, and —$SO_2$, among other groups.

The 5-isoxazolidinone ring may optionally be substituted at one or more of the positions 2, 3, and 4, wherein the substituents are the same or different, selected from the group consisting of hydrogen, alkyl, aryl, aralkyl, cycloalkyl, alkenyl, alkoxy, cyano, carboxy, carbalkoxy, carbalkoxyalkyl, carbamoyl, carbamoylalkyl, hydroxy, hydroxyalkyl, acyl, carbamoyloxy, nitro, acyloxy, aryloxy, alkylthio and alkylsulfinyl, among other groups, each which may be saturated and unsaturated and each which may be substituted.

In one embodiment, the 4-amino group is modified by acylation, alkylation and/or sulfonylation with $R_3YX$, wherein $R_3$ is selected from the group consisting of hydrogen, alkyl, aryl, aralkyl, cycloalkyl, alkenyl, alkoxy, cyano, carboxy, carbalkoxy, carbalkoxyalkyl, carbamoyl, carbamoylalkyl, hydroxy, hydroxyalkyl, acyl, carbamoyloxy, nitro, acyloxy, aryloxy, alkylthio and alkylsulfinyl, among other groups, which may be saturated and unsaturated and which may be substituted, X is halogen and acyloxy, among other groups, and Y is —CO, —$CH_2$, and —$SO_2$, among other groups.

Preferably, X=Cl, Br, I or the general group represented by formula —$OCOR_4$. Preferably, the X=a group represented by the structure of formula (IV):

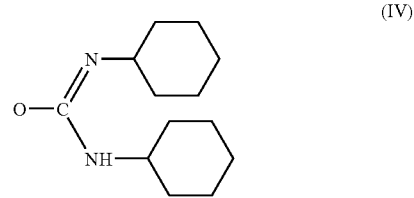

(IV)

and Y=>C=O, >$SO_2$, or >$CR_4R_5$;

wherein $R_4$, and $R_5$ are the same or different, selected from the group consisting of hydrogen, alkyl, aryl, aralkyl, cycloalkyl, alkenyl, alkoxy, cyano, carboxy, carbalkoxy, carbalkoxyalkyl, carbamoyl, carbamoylalkyl, hydroxy, hydroxyalkyl, acyl, carbamoyloxy, nitro, acyloxy, aryloxy, alkylthio and alkylsulfinyl, among other groups, each which may be saturated and unsaturated and each which may be substituted.

In another embodiment, the 4-amino group is modified by acylation, alkylation and/or sulfonylation with a compound having the general formula V:

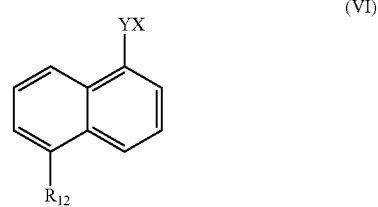

(VI)

wherein X=Cl, Br, I or the general group represented by formula IV and Y is —CO, —$CH_2$, and —$SO_2$, and $R_{12}$ is selected from the group consisting of hydrogen, alkyl, aryl, aralkyl, cycloalkyl, alkenyl, alkoxy, cyano, carboxy, carbalkoxy, carbalkoxyalkyl, carbamoyl, carbamoylalkyl, hydroxy, hydroxyalkyl, acyl, carbamoyloxy, nitro, acyloxy, aryloxy, alkylthio and alkylsulfinyl, among other groups, which may be saturated and unsaturated and which may be substituted.

Preferably, Y=>C=O, >$SO_2$, or >$CR_4R_5$ wherein $R_4$, and $R_5$ are the same or different, selected from the group consisting of hydrogen, alkyl, aryl, aralkyl, cycloalkyl, alkenyl, alkoxy, cyano, carboxy, carbalkoxy, carbalkoxyalkyl, carbamoyl, carbamoylalkyl, hydroxy, hydroxyalkyl, acyl, carbamoyloxy, nitro, acyloxy, aryloxy, alkylthio and alkylsulfinyl, among other groups, each which may be saturated and unsaturated and each which may be substituted.

Preferably, the $R_2$ [position 3] is an alkoxy, an aryloxy, or aryalkyloxy.

Since new chiral centers are created at positions 3 and 4 in 5ISOX (formula III) the products need to be separated into their purified stereoisomers. This is accompanied by various combinations of extraction and chromatography as was done for a β-lactam with six chiral centers.

Examples of the N-substituted hydroxylamines include N-methylhydroxylamine, N-hydroxyphenylglycine, N-hydroxyvaline, and N-hydroxyglycine.

Examples of alcohols include methanol, ethanol, 2-propanol, 3-methyl-2-butanol and 1-decanol.

Phenolic compounds include phenol and the cresols.

The solvent composition for the formation of ISOX is preferably about 50% pyridine and about 50% ROH. The reactions are generally carried out at room temperature and generally require from about few hours up to a few days.

Examples of reagents for side chain amino group modification included the following shown in the general formula (VI):

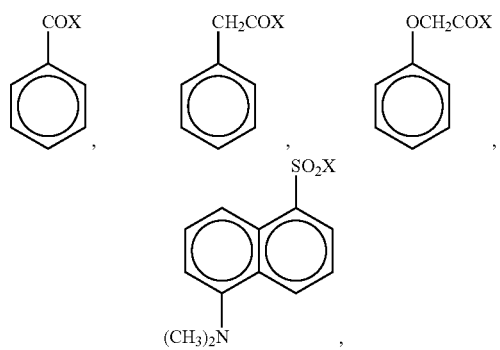

(VI)

wherein X=Cl, Br, I or the general group represented by formula —OCOR$_4$.

The respective substituent groups are now specifically described.

The alkyl group for the alkyl, which may be substituted, includes straight chain or branched C 1–10 alkyl groups (e.g. methyl, ethyl, n-propyl, isopropyl, n-butyl, isobutyl, sec-butyl, tert-butyl, n-pentyl, iso-pentyl, neopentyl, hexyl, heptyl, octyl, nonyl and decyl, among others). The preferred are straight chain or branched C 1–6 alkyl groups. The still more advantageous are straight chain or branched C 1–3 alkyl groups. The substituent on the substituted alkyl includes nitro, cyano, hydroxy, carboxy, amidino, guanidino and carbamoyl, amino that may be mono- or di-substituted by alkyl, acyl, etc., among others.

The cycloalkyl group for the cycloalkyl, which may be substituted, includes C 3–7 cycloalkyl groups. Examples of such cycloalkyl are cyclopropyl, cyclobutyl, cyclopentyl, cyclohexyl and cycloheptyl. Such cycloalkyl groups may each be substituted by, for example, nitro, cyano, hydroxy, carboxy, amidino, guanidino and carbamoyl, amino which may be mono- or di-substituted by alkyl, acyl, etc., among others.

The alkenyl group for the alkenyl, which may be substituted, includes straight-chain or branched C 2–16 alkenyl groups. The preferred alkenyl group includes allyl, vinyl, crotyl, 2-penten-1-yl, 3-penten-1-yl, 2-hexen-1-yl, 3-hexen-1-yl, 2-methyl-2-propen-1-yl and 3-methyl-2-buten-1-yl, among others. The further preferred are straight-chain or branched C 2–6 alkenyl groups. The still more advantageous are straight-chain or branched C 2–4 alkenyl groups. Such alkenyl groups may have substituents, such as nitro, cyano, amidino, guanidino, amino which may be mono- or di-substituted by alkyl, acyl, etc., and so on. The alkenyl groups mentioned above include isomers (E- and Z-forms) with respect to the double bond.

The alkoxy group for the alkoxy that may be substituted includes C 1–10 alkoxy groups, among others. As such, the alkoxy group specifically includes methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxy, cyclohexyloxy and so on. The preferred are C 1–6 alkoxy groups. The more advantageous are C 1–3 alkoxy groups. Nitro, amidino, guanidio, and amino that may be mono- or di-substituted by alkyl, acyl, etc., among others may substitute such alkoxy groups, for example.

The alkyl moiety of the alkylamino that may substitute the above alkyl, cycloalkyl, alkenyl or alkoxy group includes straight-chain or branched C 1–6 alkyl groups, among preferred examples. The preferred examples are methyl, ethyl, n-propyl, isopropyl, n-butyl, isobutyl, tert-butyl, sec-butyl, n-pentyl, isopentyl, n-hexyl, isohexyl and so on. Among others, particularly are straight-chain or branched C 1–4 alkyl groups.

The acyl moiety of the acylamino which may substitute the above alkyl, cycloalkyl, alkenyl or alkoxy group includes acyl groups derived from organic carboxylic acids, for instance. The preferred are C 1–6 alkanoyl groups, such as formyl, acetyl, propionyl, butyryl, isobutyryl, valeryl, isovaleryl, pivaloyl, hexanoyl, etc. Particularly C 1–4 alkanoyl groups are preferable.

The number of substituents on the above alkyl, cycloalkyl, alkenyl or alkoxy group may range from 1 to 6, preferably 1 to 3.

The substituted alkyl group specifically includes trifluoromethyl, trifluoroethyl, difluoromethyl, trichloromethyl, hydroxymethyl, 1-hydroxyethyl, 2-hydroxyethyl, methoxyethyl, ethoxyethyl, 1-methoxyethyl, 2-methoxyethyl, 2,2-dimethoxyethyl, 2,2-diethoxyethyl and 2-diethylphosphorylethyl, among others. The preferred are difluoromethyl, trifluoromethyl and hydroxymethyl. The more desirable is trifluoromethyl.

The substituted cycloalkyl group specifically includes 2-aminocyclopropan-1-yl, 4-hydroxycyclopentan-1-yl and 2,2-difluorocyclopentan-1-yl, among others.

The substituted alkenyl group specifically includes 3-hydroxy-2-propen-1-yl, 2-methoxyvinyl and so on.

The substituted alkoxy group specifically includes difluoromethoxy, trifluoromethoxy, 2,2,2-trifluoroethoxy, 2-methoxyethoxy, 4-chlorobenzyloxy, 2-(3,4-dimethoxyphenyl)ethoxy and so on. The preferred is difluoromethoxy.

The alkoxy moiety of the carbalkoxy group includes C 1–7 alkoxy groups (e.g. methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, etc.).

The alkoxy moiety of the carbalkoxyalkyl group includes C 1–4 alkoxy groups (e.g. methoxy, ethoxy, n-propoxy, isopropoxy, n-butoxy, isobutoxy, sec-butoxy, tert-butoxy, etc.), among others. The alkyl moiety includes C 1–4 groups (e.g. methyl, ethyl, n-propyl, isopropyl, n-butyl, isobutyl, sec-butyl, tert-butyl, etc.), among others. Specifically, carbomethoxymethyl, 2-carbomethoxyethyl, 2-carbomethoxypropyl, carboethoxymethyl, 2-carboethoxyethyl, 2-carbomethoxypropyl, 2-carbomethoxypropyl, carbopropoxymethyl, carbobutoxymethyl, etc. can be mentioned.

The alkyl moiety of the carbamoylalkyl group includes C 1–4 alkyl groups (e.g. methyl, ethyl, n-propyl, isopropyl, n-butyl, isobutyl, sec-butyl, tert-butyl, etc.).

The alkyl moiety of the hydroxyalkyl group includes C 1–7 alkyl groups (e.g. methyl, ethyl, n-propyl, isopropyl, n-butyl, isobutyl, sec-butyl, tert-butyl, n-pentyl, isopentyl, neopentyl, hexyl, heptyl, etc.)

The acyl group and the acyl moiety of the acyloxy group respectively include C 1–4 alkanoyl groups such as formyl, acetyl, propionyl, butyryl, isobutyryl and so on.

The aryl group and the aryl moiety of the aryloxy group respectively include C 6–12 aryl groups (e.g. phenyl, naphthyl, etc.).

The alkyl moiety of the alkylthio or alkylsulfinyl group includes C 1–6 alkyl group (e.g., methyl, ethyl, n-propyl, isopropyl, n-butyl, isobutyl, sec-butyl, tert-butyl, n-pentyl, isopentyl, neopentyl, hexyl, etc.).

The preferred is 5-isoxazolidinone ring which may optionally be substituted by i) an alkyl group which may be substituted, ii) cycloalkyl group which may be substituted, iii) alkenyl group which may be substituted or iv) alkoxy group which may be substituted.

Preferably, the alkyl group represented by $R_1$, includes C 1–5 alkyl groups such as methyl, ethyl, n-propyl, isopropyl, n-butyl, isobutyl, sec-butyl, tert-butyl, n-pentyl, isopentyl, neopentyl, etc. The acyl group represented by $R_1$ includes C 1–4 acyl groups such as C 1–4 alkanoyl group etc. The carbalkoxy group represented by R1 includes those having C 1–4 alkoxy groups such as formyl, acetyl, propionyl, butyryl, isobutyryl, etc. The alkylcarbamoyl and dialkylcarbamoyl groups represented by R1 respectively include those having C 1–4 alkyl moieties such as methyl, ethyl, n-propyl, isopropyl, n-butyl, isobutyl, sec-butyl, tert-butyl, etc. The alkylsulfonyl group represented by $R_1$ includes those having C 1–4 alkyl moieties such as those mentioned just above. $R_1$ is preferably hydrogen.

Preferably, $R_3$ is selected from the group consisting of straight and branched alkylene groups having 1 to 4 carbon atoms, whereby at most one methylene group is present between X and the pyridyl group. Preferably, $R_5$ is $CH_2$.

The alkyl group represented by $R_2$ includes straight chain or branched C 1–10 alkyl groups (e.g. methyl, ethyl, n-propyl, isopropyl, n-butyl, isobutyl, sec-butyl, tert-butyl, n-pentyl, isopentyl, neopentyl, hexyl, heptyl, octyl, nonyl, decyl, etc.). Among these alkyl groups, straight-chain or branched C 1–6 alkyl groups to are preferred, and straight-chain or branched C 1–3 alkyl groups are particularly desirable.

The alkoxy group represented by $R_2$, includes C 1–10 alkoxy groups (e.g. methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, etc.). The preferred are C 1–6 alkoxy groups. The more desirable are C 1–3 alkoxy groups.

The alkoxy moiety of the alkoxyalkoxy group represented by $R_2$ includes C 1–4 alkoxy groups (e.g. methoxy, ethoxy, n-propoxy, isopropoxy, n-butoxy, isobutoxy, sec-butoxy, tert-butoxy, etc.).

The alkyl group represented by $R_3$ is preferably a C 1–4 alkyl group (e.g. methyl, ethyl, n-propyl, isopropyl, n-butyl, isobutyl, sec-butyl, tert-butyl, etc.).

The substituent group of the substituted hydrocarbon group is preferably a C 1–3 hydrocarbon group such as C 1–6 straight-chain or branched alkyl groups (e.g. methyl, ethyl, propyl, isopropyl, butyl, isobutyl, sec-butyl, pentyl, isopentyl, hexyl, etc.), C 2–6 alkenyl groups (e.g. vinyl, allyl, 2-butenyl, methylallyl, 3-butenyl, 2-pentenyl, 4-pentenyl, 5-hexenyl, etc.), C 2–6 alkinyl groups (e.g. ethynyl, propargyl, 2-butin-1-yl, 3-butin-2-yl, 1-pentin-3-yl, 3-pentin-1-yl, 4-pentin-2-yl, 3-hexin-1-yl, etc.), C 2–6 cycloalkyl groups (e.g. cyclopropyl, cyclobutyl, cyclopentyl, cyclohexyl, etc.), C 3–6 cycloalkenyl groups (e.g. cyclobutenyl, cyclopentenyl, cyclohexenyl, cyclohexadienyl, etc.), and C 7–13 aralkyl groups (e.g. benzyl, 1-phenethyl, 2-phenethyl, etc.), and C 6–10 aryl groups (e.g. phenyl, naphthyl, etc.), and so on. Among others, straight-chain or branched C 1–6 alkyl groups (e.g. methyl, ethyl, propyl, isopropyl, butyl, isobutyl, sec-butyl, pentyl, isopentyl, hexyl, etc.) are preferred. Particularly, straight-chain or branched C 1–4 alkyl groups are preferred.

The substituent group of the substituted hydrocarbon group may include, among others, C 6–10 aryl groups (e.g. phenyl, naphthyl, etc.), amino, C 1–6 alkylamino (e.g. methylamino, ethylamino, isopropylamino, etc.), di-C 1–6 alkylamino (e.g. dimethylamino, diethylamino, etc.), azide, nitro, hydroxy, C 1–4 alkoxy (e.g. methoxy, ethoxy, propoxy, butoxy, etc.), C 6–10 aryloxy (e.g. phenoxy, naphthyloxy, etc.), C 1–6 alkylthio (e.g. methylthio, ethylthio, propylthio, etc.), C 6–10 arylthio (e.g. phenylthio, naphthylthio, etc.), cyano, carbamoyl, carboxy, C 1–4 alkoxycarbonyl (e.g. methoxycarbonyl, ethoxycarbonyl, etc.), C 7–11 aryloxycarbonyl (e.g. phenoxycarbonyl, 1-naphthyloxycarbonyl, 2-naphthyloxycarbonyl, etc.), carboxy-C 1–4 alkoxy (e.g carboxymethoxy, 2-carboxyethoxy, etc.), C 1–6 alkanoyl (e.g. formyl, acetyl, propionyl, isopropionyl, butyryl, pentanoyl, hexanoyl, etc.), C 7–11 aroyl (e.g. benzoyl, 1-naphthoyl, 2-naphthoyl, etc.), C 6–10 arylsulfonyl (e.g. benzenesulfonyl, 1-naphthylsulfonyl, 2-naphthylsulfonyl, etc.), C 1–6 alkylsulfinyl (e.g. methylsulfinyl, ethylsulfinyl, etc.), C 6–10 arylsulfinyl (e.g. benzenesulfinyl, 1-naphthylsulfinyl, 2-naphthylsulfinyl, etc.), C 1–6 alkylsulfonyl (e.g. methylsulfonyl, ethylsulfonyl, etc.), 5- or 6-membered heterocyclic groups having 1 to 4 hetero-atoms (e.g. N, O, S, etc.) (e.g. 2-furyl, 2-thienyl, 4-thiazolyl, 4-imidazolyl, 4-pyridyl, 1,3,4-thiadiazol-2-yl, 1-methyl-5-tetrazolyl, etc.), 5- or 6-membered heterocyclic carbonyl groups having 1 to 4 hetero-atoms (e.g. N, O, S) (e.g. 2-froyl, 2-thenoyl, nicotinyl, isonicotinyl, etc.) and 5- or 6-membered heterocyclic thio groups having 1 to 4 hetero-atoms (e.g. N, O, S, etc.) (e.g. 4-pyridylthio, 2-pyrimidylthio, 1,3,4-thiadiazol-2-ylthio, 1-methyl-5-tetrazolythio, etc.). The heterocyclic thio groups may each form a bicyclic structure with a benzene ring (e.g. 2-benzothiazolylthio, 8-quinolylthio, etc.).

In one preferred embodiment, the substituent on position 2 is 2-substituted 3-methylbutanoic acid. In another preferred embodiment, the substituent on position 3 is 2-methylpropoxy. In another preferred embodiment, the substituent on position 4 is phenoxyacetamido.

Illustrative compounds according to the invention are:

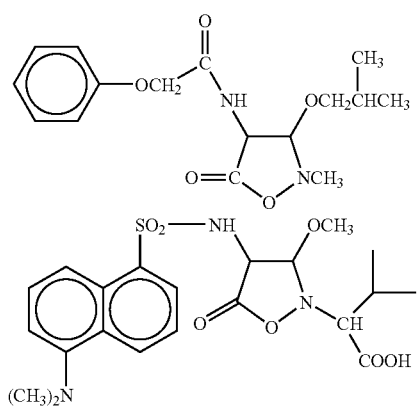

-continued

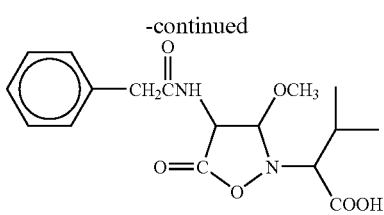

or an enantiomer, diastereomer or pharmaceutically acceptable salt thereof.

Since new chiral centers are created in the synthesis at positions 3 and 4 in 5ISOX (formula III) the products need to be separated into their purified stereomers. This is accompanied by various combinations of extraction and chromatography as was done for a β-lactam with six chiral centers. The Wang methodology led to pure crystalline isomers of β-lactams that had multiple chiral centers.

The 5-isoxazolidinone compounds can be used in the form of a pharmaceutically acceptable salt. The physiologically acceptable salt includes salts with inorganic bases, salts with organic bases, and salts with basic amino acids. Among the inorganic bases mentioned above are alkali metals (e.g. sodium, potassium, etc.) and alkaline earth metals (e.g. calcium, magnesium, etc.). The organic bases may be trimethylamine, triethylamine, pyridine, picoline, N,N-dibenzylethylenediamine, ethanolamine, diethanolamine, trishydroxymethylaminomethane, dicyclohexylamine, etc. The basic amino acids may be arginine, lysine and so on. The production processes well known in the art can produce these salts.

Depending on the process conditions and the starting materials, the end product obtained in production of the product is either as the free base or in the acid addition salt, both of which are included within the scope of the invention. Thus, basic, neutral or mixed salts may be obtained as well as hemi, mono, sesqui or polyhydrates. The acid addition salts of the new compounds may in a manner known per se be transformed into free base using basic agents such as alkali or by ion exchange. On the other hand, the free bases obtained may form salts with organic or inorganic acids. In the preparation of acid addition salts preferably such acids are used which form suitable therapeutically acceptable salts. Such acids include hydrohalogen acids, sulfonic, phosphoric, nitric, and perchloric acids; aliphatic, alicyclic, aromatic, heterocyclic carboxy or sulfonic acids, such as formic, acetic, propionic, succinic, glycolic, lactic, malic, tartaric, citric, ascorbic, maleic, hydroxymaleic, pyruvic, phenylacetic, benzoic, p-aminobenzoic, antranilic, p-hydroxybenzoic, salicylic or p-aminosalicylic acid, embonic, methanesulfonic, ethanesulfonic, hydroxyethanesulfonic, ethylenesulfonic, halogenbenzenesulfonic, toluenesulfonic, naphthylsulfonic or sulfanilic acids; methionine, tryptophane, lysine or arginine.

The composition can comprise, in addition to one or more 5-isoxazolidinone compounds, compounds and/or compositions that will also aid in the treatment of bacterial infections in dosages useful for the treatment of infections, as known to those skilled in the art.

Dosages for the above-mentioned additional compounds are established and known to those skilled in the art.

The term "treatment", as used herein, unless otherwise indicated, includes the treatment or prevention of a bacterial infection as provided in the method of the present invention.

"Ameliorate" or "amelioration" means a lessening of the detrimental effect or severity of infection in the subject receiving therapy, the severity of the response being determined by means that are well known in the art.

"Therapeutically effective amount" means that the amount of antibacterial agent used for administration is sufficient to ameliorate the clinical symptoms of bacterial infection or to otherwise reduce the severity of or prevent further bacterial damage. Therapeutically effective amounts will differ based upon the nature of the patient, the degree and severity of the disease, the clinical setting, the mode of administration, and the like and can be determined empirically by the skilled practitioner without undue experimentation.

"Therapeutic" as used herein refers to those agents effective in the prevention or treatment of a disorder or pathologic physiological condition.

"Treat," "treating," "treatment," and "therapy" as used herein refer to any curative therapy, prophylactic therapy, ameliorative therapy and preventative therapy.

As used herein, unless otherwise indicated, the terms "bacterial infection(s)" include bacterial infections that occur in mammals, fish and birds as well as disorders related to bacterial infections that may be treated or prevented by administering antibiotics such as the compounds of the present invention. Such bacterial infections, and disorders related to such infections, include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus*, or *Peptostreptococcus* spp.; pharyngitis, rheumatic fever, and glomerulonephritis related to infection by *Streptococcus pyogenes*, Groups C and G *streptococci, Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive *staphylococci* (i.e., *S. epidermidis, S. hemolyticus*, etc.), *Streptococcus pyogenes, Streptococcus agalactiae*, Streptococcal groups C–F (minute-colony *streptococci*), viridans *streptococci, Corynebacterium minutissimum, Clostridium* spp., or *Bartonella henselae*; uncomplicated acute urinary tract infections related to infection by *Staphylococcus saprophyticus* or *Enterococcus* spp.; *urethritis* and *cervicitis*; and sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and Toxic shock syndrome), or Groups A, B, and C *streptococci*; ulcers related to infection by *Helicobacter pylori*; systemic febrile syndromes related to infection by *Borrelia recurrentis*; Lyme disease related to infection by *Borrelia burgdorferi; conjunctivitis, keratitis*, and *dacrocystitis* related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; odontogenic infection related to infection by viridans *streptococci*; persistent cough related to infection by *Bordetella pertussis*; gas gangrene related to infection by *Clostridium perfringens* or *Bacteroides* spp.; and atherosclerosis related to infection by *Helicobacter pylori* or *Chlamy*- dia pneumoniae. Bacterial infections and protozoa infections and disorders related to such infections that may be treated or prevented in animals include the following: bovine respiratory disease related to infection by *P. haem., P. multocida, Mycoplasma bovis,* or *Bordetella* spp.; cow enteric disease related to infection by *E. coli* (i.e., *coccidia, cryptosporidia,* etc.); dairy cow mastitis related to infection by *Staph. aureus, Strep. uberis, Strep. agalactiae, Strep. dysgalactiae, Klebsiella* spp., *Corynebacterium,* or *Enterococcus* spp.; swine respiratory disease related to infection by *A. pleuro., P. multocida,* or *Mycoplasma* spp.; swine enteric disease related to infection by *E coli, Lawsonia intracellularis, Salmonella,* or *Serpulina hyodyisinteriae*; cow footrot related to infection by *Fusobacterium* spp.; cow metritis related to infection by *E coli*; cow hairy warts related to infection by *Fusobacterium necrophorum* or *Bacteroides nodosus*; cow pink-eye related to infection by *Moraxella bovis*; urinary tract infection in dogs and cats related to infection by *E coli*; skin and soft tissue infections in dogs and cats related to infection by *Staph. epidermidis, Staph. intermedius, coagulase neg. Staph.* or *P. multocida*; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas,* or *Prevotella*. Other bacterial infections and disorders related to such infections that may be treated or prevented in accord with the method of the present invention.

The compounds of the present invention, and the pharmaceutically acceptable salts thereof (hereinafter "the active compounds"), may be administered through oral, parenteral, topical, or rectal routes in the treatment of bacterial infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 0.5% to about 99% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical technique will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol or polyethyleneoxide-polylysine substituted with palmitoylresidues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The compounds of the present invention, and the pharmaceutically acceptable salts thereof (hereinafter "the active compounds"), may be administered through oral, parenteral, topical, or rectal routes in the treatment of bacterial and protozoal infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc.

Moreover, oral pharmaceutical compositions can be suitably sweetened and/or flavored. In general, the active compounds are present in such dosage forms at concentration levels ranging from about 5.0% to about 99% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol or polyethyleneoxide-polylysine substituted with palmitoylresidues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The compound should be administered such that a therapeutically effective concentration of the compound is in contact with the affected cells of the body. The dose administered to an animal, particularly a human, in the context of the present invention should be sufficient to effect a therapeutic response in the animal over a reasonable period of time. The dose will be determined by the strength of the particular compound employed and the condition of the animal, as well as the body weight of the animal to be treated. The existence, nature, and extent of any adverse side effects that might accompany the administration of a particular compound also will determine the size of the dose and the particular route of administration employed with a particular patient. In general, the compounds of the present invention are therapeutically effective at low doses. The effective dose range is from about 0.01 mM to about 10 mM. Accordingly, the compounds will be generally administered in low doses.

The pharmaceutically acceptable salts of the compound of this invention include the conventional non-toxic salts as formed, from non-toxic inorganic or organic bases. For example, such conventional non-toxic salts include those derived from inorganic bases such as an alkali or alkaline earth metal hydroxide, e.g., potassium, sodium, lithium, calcium, or magnesium, and the like: and the salts prepared from organic bases such as an amine, e.g., dibenzylethylenediamine, trimethylamine, piperidine, pyrrolidine, benzylamine and the like, or a quaternary ammonium hydroxide such as tetramethylammonium hydroxide and the like. The pharmaceutically acceptable salts can be synthesized from the compounds of this invention by conventional chemical methods. Generally, the salts are prepared by reacting the free acid with stoichiometric amounts or with an excess of the desired salt-forming inorganic or organic base in a suitable solvent or various combinations of solvents.

The compound of the invention can be formulated in pharmaceutical compositions by combining the compound with a pharmaceutically acceptable carrier. Examples of such carriers are set forth below.

The compound may be employed in powder or crystalline form, in liquid solution, or in suspension. It may be administered by a variety of means; those of principal interest include: topically, orally and parenterally by injection (intravenously or intramuscularly).

Compositions for injection, one route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the Compound, the virulence of the infection and other factors. Such matters, however, are left to the routine discretion of the physician according to principles of treatment well known in the antibacterial arts.

The compositions for administration to humans per unit dosage, whether liquid or solid, may contain from about 0.01% to as high as about 99% of Compound I, one embodiment of the range being from about 10–60%. The composition will generally contain from about 15 mg to about 2.5 g of Compound I, one embodiment of this range being from about 250 mg to 1000 mg. In parenteral administration, the unit dosage will typically include pure Compound I in sterile water solution or in the form of a soluble powder intended for solution, which can be adjusted to neutral pH and isotonicity.

The invention described herein also includes a method of treating a bacterial infection in a mammal in need of such treatment comprising the administration of Compound I to the mammal in an amount effective to treat the infection.

One embodiment of the methods of administration of Compound I includes oral and parenteral methods, e.g., i.v. infusion, i.v. bolus and i.m. injection.

For adults, about 5–50 mg of Compound I per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

Compound I is an antibacterial agent active against *Pseudomonas aeruginosa* isolates resistant to various antibiotics. Many antibacterial agents are susceptible to attack by a renal enzyme known as dehydropeptidase (DHP). This attack or degradation may reduce the efficacy of the antibacterial agent. The compound of the present invention, on the other hand, is less subject to such attack, and therefore may not require the use of a DHP inhibitor.

Compound I of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenem and disclose suitable inhibitors, combination compositions and methods of treatment. A preferred weight ratio of Compound I: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

Under certain conditions, the effectiveness of oral compositions of 5-isoxazolidinones and its salts and esters can be improved if such compositions contain a buffering agent or an enteric coating agent such that the compounds of the invention do not have prolonged contact with highly acidic gastric juice. Such buffered or enterically coated compositions may be prepared in accordance with conventional pharmaceutical practice.

The 5-isoxazolidinones or its salt or ester may be present in the composition as sole therapeutic agent or it may be present together with other therapeutic agents such as a .beta.-lactam antibiotic. Suitable .beta.-lactam antibiotics for inclusion in such synergistic compositions include not only those known to be highly susceptible to .beta.-lactamases but also those which have a good degree of intrinsic resistance to .beta.-lactamases. Thus, suitable .beta.-lactam antibiotics for inclusion in the compositions of this invention include benzylpenicillin, phenoxymethylpenicillin, carbenicillin, methicillin, propicillin, ampicillin, amoxycillin, epicillin, ticarcillin, cyclacillin, 6-aminopenicillanic acid, 7-aminocephalosporanic acid, 7-aminodesacetoxycephalosporanic acid, cephaloridine, cephalothin, cefazolin, cephalexin, cefoxitin, cephacetrile, cephamandole, cephapirin, cephradine, cephaloglycine and other well known penicillins and cephalosporins or pro-drugs therefor such as hetacillin, metampicillin, the acetoxymethyl, pivaloyloxymethyl or phthalidyl esters of benzylpenicillin, ampicillin, amoxycillin or cephaloglycine or the phenyl, tolyl or indanyl α-esters of carbenicillin or ticarcillin or the like.

When present in a pharmaceutical composition together with a .beta.-lactam antibiotic, the ratio of 5-isoxazolidinones or its salt or ester present to .beta.-lactam antibiotic present may be from, for example, 20:1 to 1:12, more usually 10:1.

The total quantity of antibacterial agents present in any unit dosage form will normally be between 50 and 1500 mg and will usually be between 100 and 1000 mg.

Compositions of this invention may be used for the treatment of infections of inter alia, the respiratory tract, the urinary tract and soft tissues in humans. Compositions of this invention may also be used to treat infections of domestic animals such as mastitis in cattle.

Normally between 50 and 6000 mg of the compositions of the invention will be administered each day of treatment but more usually between 500 and 3000 mg. of the composition of the invention will be administered per day. However for the treatment of severe systemic infections or infections of particularly intransigent organisms, higher doses may be used in accordance with clinical practice. The exact form of the compositions of this invention will depend to some extent on the microorganism that is being treated. For treatment of most infections the compositions of this invention are normally adapted to produce a peak blood level of at least 0.1 μg/ml, more suitably at least 0.25 μg/ml, and preferably at least 1 μg/ml of synergist, for example, 2.5–5 μg/ml. of synergist.

The penicillin of cephalosporin in synergistic compositions of this invention will normally be present by up to or at approximately the amount conventionally used when that penicillin or cephalosporin is the sole therapeutic agent used in the treatment of infection.

Particularly favored compositions of this invention will contain from 150–1000 mg of amoxycillin, ampicillin or a pro-drug thereof and from 50–500 mg of 5-isoxazolidinones or a salt or in-vivo hydrolysable ester thereof and more suitably from 200–500 mg of amoxycillin, ampicillin or a pro-drug thereof and from 50–250 mg of 5-isoxazolidinones or a salt or in-vivo hydrolysable ester thereof.

The materials present in such compositions may be hydrated if required. The weights of the antibiotics in such composition are expressed on the basis of antibiotic theoretically available from the composition and not on the basis of the weight of pro drug.

When used herein the term "pro-drug" of an antibacterially active drug means any medicament which is known to be converted in the body to the antibacterially active drug per se.

This invention also provides a method of treating bacterial infection in a mammal which method comprises administering to the mammal an antibacterially effective amount of 5-isoxazolidinones or a salt or ester thereof. Most suitably a pharmaceutically acceptable salt or in vivo hydrolysable ester of 5-isoxazolidinones is used.

This invention also provides a method of treating bacterial infection in a mammal, which method comprises administering to the mammal a synergistically effective amount of 5-isoxazolidinones or a salt or ester thereof and an antibacterially effective amount of a .beta.-lactam antibiotic. Most suitably a pharmaceutically acceptable salt or in-vivo hydrolysable ester of 5-isoxazolidinones is used.

A further aspect of this invention provides a method of treating infections in humans caused by *Klebsiella aeroginosa*, which method comprises administering to an infected human a daily dose of (a) at least 500 mg of ampicillin, amoxycillin or a pro-drug for ampicillin or amoxycillin, and (b) at least 100 mg of 5-isoxazolidinones or a salt or in-vivo hydrolysable ester thereof.

The penicillin and synergist may be administered in separate compositions or in synergistic compositions containing both components. Normally the daily dose of the antibiotics will be administered in divided form, for example, as 2 to 5 doses per day. Usually the antibiotics will be administered as 3 or 4 doses per day.

The penicillin used in this treatment may be anhydrous ampicillin, ampicillin trihydrate, sodium ampicillin, hetacillin, pivampicillin hydrochloride talampicillin hydrochloride, amoxycillin trihydrate, sodium amoxycillin or the like. Each unit dose will usually contain from 200–1000 mg of the penicillin, for example, 250 to 500 mg.

The synergist used in this treatment will generally be a salt or in-vivo hydrolysable ester of 5-isoxazolidinones such as the sodium or potassium salt of 5-isoxazolidinones or the acetoxymethyl, pivaloyloxymethyl, phthalidyl or like ester of 5-isoxazolidinones. Each unit dose will usually contain from 50 to 500 mg of the synergist, for example, 100 to 250 mg.

A further aspect of this invention provides a method of treating infections in humans caused by *Pseudomonas aeroginosa*, which method comprises administering to an infected human a daily dose of at least 1 g. of carbenicillin or ticarcillin or a pro-drug for carbenicillin or ticarcillin and (b) at least 0.5 g. of 5-isoxazolidinones or a salt or in-vivo hydrolysable ester thereof.

The penicillin and synergist may be administered in separate compositions or synergistic compositions containing both components. Normally, the daily dose of antibiotics will be administered in divided form, for example, as 2 to 5 doses per day. Usually the antibiotics will be administered as 3 or 4 doses per day. For systemic or several infections the compositions will be adapted for administration by injection or infusion. For infections of the urinary tract the compositions may be adapted for administration orally or by injection or infusion.

The penicillin used in this treatment may be carbenicillin, carbenicillin α-phenyl ester, carbenicillin α-5-indanyl ester, ticarcillin, ticarcillin α-tolyl ester, ticarcillin α-phenyl ester and like, and will usually be in the form of a salt such as a sodium salt. Each unit dose will usually contain from 400 to 4000 mg of the penicillin, for example, 500 to 1000 mg.

The synergist used in this treatment will suitably be the sodium or potassium salt of 5-isoxazolidinones or an in-vivo hydrolysable ester thereof, such as the acetoxymethyl, pivaloyloxymethyl or phthalidyl ester of 5-isoxazolidinones.

Each unit dose will usually contain from 200 to 1000 mg of the synergist, for example, 250 to 750 mg.

A further aspect of this invention provides a method of treating infections in the respiratory tract of humans, which method comprises administering to an infected human a daily dose of (a) at least 500 mg of amoxycillin or ampicillin or a pro-drug for ampicillin or amoxycillin, and (b) at least 100 mg of 5-isoxazolidinones or a salt or in-vivo hydrolysable ester thereof.

Especially suitable doses and methods of administration are similar to those described for the treatment of infections due to *Klebsiella aeroginosa*.

A further aspect of this invention provides a method of treating infections in the urinary tract in humans which method comprises administering to an infected human a daily dose of (a) at least 500 mg of ampicillin, amoxycillin, carbenicillin, ticarcillin, cephalothin, cephaloridine, cephaloglycine, cephalexin, cefazolin, cephapirin or cephradine or cephradine or a pro-drug for such medicaments and (b) at least 100 mg of the compound of formula I or a salt or in-vivo hydrolysable ester thereof.

The preferred embodiments are exemplified by the following examples.

EXAMPLES

Example 1

Synthesis of a 5-ISOX from N-hyroxyvaline, methanol and phenylacetic acid:

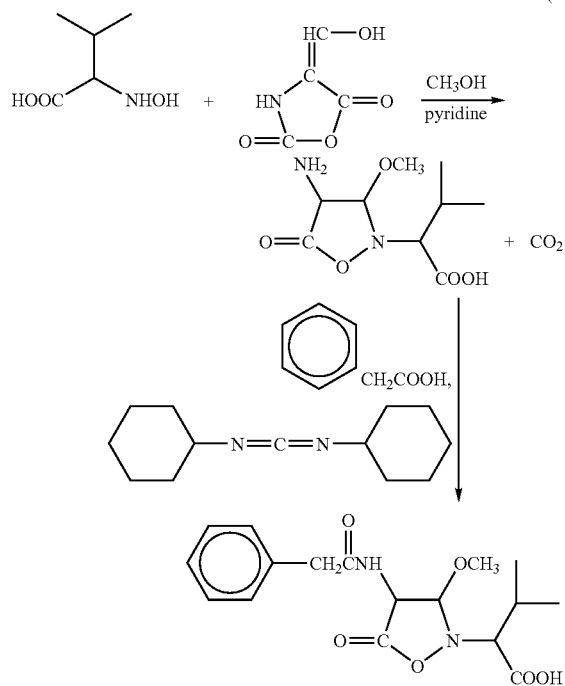

(VII)

Example 2

Synthesis of a 5ISOX from N-methylhydroxylamine, isobutanol and phenoxyacetic acid:

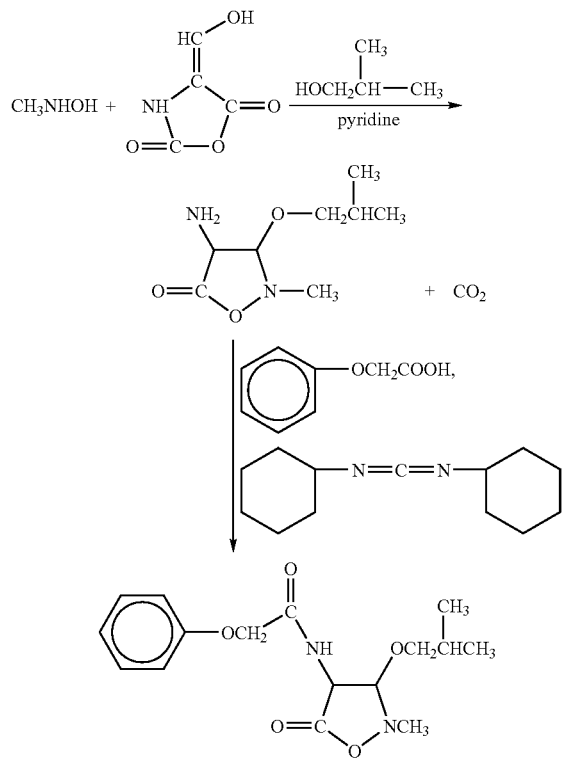

Example 3

Synthesis of a 5ISOX from N-hydroxyvaline, methanol and dansyl chloride:

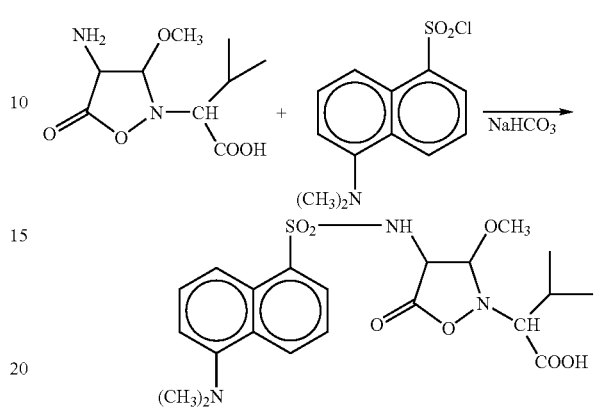

Without wishing to be bound by any theory, it is believed that the 5ISOX interacts with the "penicillin interactive proteins" (See Koch, op. cit., for a definition of this term). Thus 5ISOX have been postulated and demonstrated in this laboratory to target cell wall synthesis in bacteria as with the β-lactams. These studies have shown that various 5ISOX possess two attributes critical to this discovery: (1) the 5ISOX bind to PBPs of bacteria; and (2) the 5ISOX inhibit β-lactamases, including, importantly, the metallo-β-lactamases, Class B.

The mode of action is postulated to be analogous to that of 4-alkoxy-azetidin-2-ones(AAZ) that cross-link two amino acid residues in the active site of a Class A β-lactamase. See Ahluwalia et al., Biochem. Biophys. Res. Commun. 206, 577–583 (1995). Several hundred AAzs were screened against a panel of Gram (+) and Gram (−) bacteria; minimum inhibitory concentrations (MIC) of less than 1 μg/ml was seen for most of the AAZs and below 1 ng/ml for several. An MIC<1 ng/ml was seen against *M. tuberculosis*. See Day, "Cross-linking as a tool in Analyzing Protein Comlexes" in Pandalai, Ed., *Recent Research Developments in Protein Engineering* in press (2001). This underscores the importance of the OR group on the reactivity of the nominal aldehydic center in both AAZs and 3-position of 5ISOX. The failure of Panfil et al., op. cit. (1998) to see significant growth inhibition may be due to lack of the 3-OR substituent.

The description fully satisfies the objects, aspects and advantages set forth. While the invention has been set forth in conjunction with specific embodiments thereof, it is evident that many alternatives, modifications, and variations will be apparent to those skilled in the art in the light of the foregoing description. Accordingly, it is intended to embrace all such alternatives, modifications, and variations which fall within the spirit and scope of the following claims.

The invention claimed is:

1. A pharmaceutical composition which comprises:
   a. a 5-isoxazolidinone compound, a pharmaceutically acceptable salt thereof, or an in-vivo-hydrolysable ester thereof, having the general formula (II):

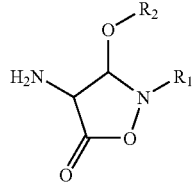

wherein $R_1$, and $R_2$, are the same or different, selected from the group consisting of: (a) hydrogen; (b) alkyl, aryl, aralkoxy, aralkyl, cycloalkyl, alkynyl, alkenyl, alkoxy, carboxy, carbalkoxy, carbalkoxyalkyl, carbamoyl, carbamoylalkyl, hydroxy, hydroxyalkyl, acyl, carbamoyloxy, acyloxy, aryloxy, alkylthio, alkylsulfinyl, cycloalkyl, cycloalkylalkyl, cycloalkenyl, cycloalkenylalkyl, isomeric alkyl among other groups, each which may be saturated and unsaturated and each which may be substituted with $Z_1$, $Z_2$ and $Z_3$; (c) halogen; (d) hydroxyl; (e) cyano; (f) nitro; (g) —C(O)H or —C(O)$R_6$; (h) —$CO_2$H or —$CO_2R_6$; (i) -$Z_4$-$NR_7R_8$; or (j) -$Z_4$-N($R_{11}$)-$Z_5$-$NR_9R_{11}$;

wherein $R_6$, $R_7$, $R_8$, $R_9$, $R_{10}$, and $R_{11}$, are each independently (a) hydrogen; or (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z_1$, $Z_2$ and $Z_3$;

wherein $Z_1$, $Z_2$ and $Z_3$ are each independently (a) hydrogen; (b) halo; (c) hydroxy; (d) alkyl; (e) alkenyl; (f) aryl; (g) aralkyl; (h) alkoxy; (i) aryloxy; (j) aralkoxy; (k) heterocycle, substituted heterocycle or heterocyclooxy; (l) —SH, —S(O)n $Z_4$, —S(O)m—OH, —S(O)m—$OZ_4$, —O—S(O)m-$Z_4$, —O—S(O)m $Z_4$—O—S(O)m OH or —O—S(O)m—$OZ_4$; (m) oxo; (n) nitro; (o) cyano; (p) —C(O)H or —C(O)$Z_4$; (q) —$CO_2$H or —$CO_2Z_4$; and wherein $Z_4$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy, trihaloalkoxy, dialkylaminocarbonyl, alkylcarbonylamino, arylalkoxy, aryloxyalkyl, alkylaryloxyalkyl and heterocycle; and substituted compounds thereof; and b. a pharmaceutically acceptable diluent or carrier.

2. A pharmaceutical composition which comprises:

a. a 5-isoxazolidinone derivative compound, a pharmaceutically acceptable salt thereof, or an in-vivo-hydrolysable ester thereof having the general formula (III):

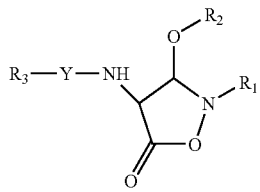

wherein $R_1$, $R_2$, and $R_3$ are the same or different, selected from the group consisting of: (a) hydrogen; (b) alkyl, aryl, aralkoxy, aralkyl, cycloalkyl, alkynyl, alkenyl, alkoxy, carboxy, carbalkoxy, carbalkoxyalkyl, carbamoyl, carbamoylalkyl, hydroxy, hydroxyalkyl, acyl, carbamoyloxy, acyloxy, aryloxy, alkylthio, alkylsulfinyl, cycloalkyl, cycloalkylalkyl, cycloalkenyl, cycloalkenylalkyl, among other groups, each which may be saturated and unsaturated and each which may be substituted with $Z_1$, $Z_2$ and $Z_3$; (c) halogen; (d) hydroxyl; (e) cyano; (f) nitro; (g) —C(O)H or —C(O)$R_6$; (h) —$CO_2$H or —$CO_2R_6$; (i) -$Z_4$-$NR_7R_8$; or (j) -$Z_4$-N($R_{11}$)-$Z_5$-$NR_9R_{11}$;

wherein $R_6$, $R_7$, $R_8$, $R_9$, $R_{10}$ and $R_{11}$, are each independently (a) hydrogen; or (b) alkyl, alkenyl. alkynyl, alkoxy, cycloalkyl, cycloalkylalkyl, cycloalkenyl, cycloalkenylalkyl, aryl, aryloxy, aralkyl or aralkoxy, any of which may be substituted with $Z_1$, $Z_2$, and $Z_3$;

wherein $Z_1$, $Z_2$ and $Z_3$ are each independently (a) hydrogen; (b) halo; (c) hydroxy; (d) alkyl; (e) alkenyl; (f) aryl; (g) aralkyl; (h) alkoxy; (i) aryloxy; (j) aralkoxy; (k) heterocycle, substituted heterocycle or heterocyclooxy; (l) —SH, —S(O)n$Z_4$, —S(O)m—OH, —S(O)m—$OZ_4$, —O—S(O)m-$Z_4$, —O—S(O)m-$Z_4$, —O—S(O)m OH or —O—S(O)m—$OZ_4$; (m) oxo; (n) nitro; (o) cyano; (p) —C(O)H or —C(O)$Z_4$; (q) —$CO_2$H or —$CO_2Z_4$; and wherein $Z_4$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy, trihaloalkoxy, dialkylaminocarbonyl, alkylcarbonylamino, arylalkoxy, aryloxyalkyl, alkylaryloxyalkyl and heterocycle; and substituted compounds thereof; and wherein Y is selected from the group consisting of Cl, Br, I and the general group represented by formula —$OCOR_4$; and b. a pharmaceutically acceptable diluent or carrier.

3. A pharmaceutical composition according to claim 2 in a form suitable for oral administration.

4. A pharmaceutical composition according to claim 2 in a form suitable for administration by injection or infusion.

5. The pharmaceutical composition of claim 2, wherein the 5-isoxazolidinones or a pharmaceutically acceptable salt thereof is in a form adapted for administration with an antibacterial agent.

6. A method for producing an antibacterial effect in a mammal in need of such treatment, which comprises administering to the mammal an effective amount of a compound as described in claim 1, a pharmaceutically-acceptable salt thereof, or an in-vivo-hydrolysable ester thereof.

7. A method for producing an antibacterial effect in a mammal in need of such treatment, which comprises administering to the mammal an effective amount of a compound as described in claim 1, a pharmaceutically-acceptable salt thereof, or an in-vivo-hydrolysable ester thereof.

* * * * *